United States Patent [19]

Rudolph et al.

[11] 4,005,137

[45] Jan. 25, 1977

[54] PROCESS FOR THE PURIFICATION AND SEPARATION OF PERHALOALKANOIC ACIDS FROM MIXTURES THEREOF WITH PERHALOALKANES

[75] Inventors: Werner Rudolph, Anderten, Hannover; Joachim Massonne, Hannover, both of Germany

[73] Assignee: Kali-Chemie Aktiengesellschaft, Hannover, Germany

[22] Filed: Feb. 10, 1975

[21] Appl. No.: 548,818

[30] Foreign Application Priority Data

Feb. 19, 1974 Germany ................. 2407834

[52] U.S. Cl. .............. 260/539 R; 260/653.1 T
[51] Int. Cl.² .................. C07C 5/42; C07C 53/34
[58] Field of Search ................. 260/539 R

[56] References Cited
UNITED STATES PATENTS 3,040,081   6/1962   Barie et al. ................. 260/539 R

*Primary Examiner*—Jane S. Myers
*Attorney, Agent, or Firm*—Michael J. Striker

[57] ABSTRACT

Processes for the separation and purification of a perhaloalkanoic acid or mixture of perhaloalkanoic acids having the formula

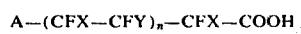
$$A-(CFX-CFY)_n-CFX-COOH$$

in which A is a perfluoromethyl, perfluoroethyl, perfluoropropyl or perfluoroisopropyl radical, X is a fluoro or a trifluoromethyl radical, Y is a fluoro or chloro radical, and $n$ is an integer from 1 to 4, from a mixture containing the said acid or mixture of acids and a perhaloalkane or mixture of perhaloalkanes having the formula

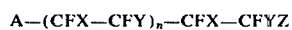
$$A-(CFX-CFY)_n-CFX-CFYZ$$

in which formula A, X, Y and $n$ have the same significance as in the previous formula and Z is an iodo, chloro or bromo radical, which comprises adsorbing the said mixture in the form of a liquid upon a chromatographic column of adsorbent silica gel particles and subsequently eluting the perhaloalkane or perhaloalkanes therefrom with a weakly polar eluent and subsequently eluting the perfluoroalkanoic acid or acids therefrom with a strongly polar eluent.

6 Claims, No Drawings

PROCESS FOR THE PURIFICATION AND SEPARATION OF PERHALOALKANOIC ACIDS FROM MIXTURES THEREOF WITH PERHALOALKANES

BACKGROUND OF THE INVENTION

Perhaloalkanoic acids having the formula $$A-(CFX-CFY)_n-CFX-COOH$$

in which A is a perfluoromethyl, perfluoroethyl, perfluoropropyl or perfluoroisopropyl radical, X is a fluoro or a trifluoromethyl radical, Y is a fluoro or chloro radical, and n is an integer from 1 to 4, and mixtures of such perhaloalkanoic acids, are valuable intermediates for the production of compounds that are surfactants.

Starting materials for the production of these perhaloalkanoic acids or mixtures thereof are perhaloalkanes having the formula $$A-(CFX-CFY)_n-CFX-CFYZ$$

in which A, X, Y and n have the same significance as in the foregoing formula and Z is an iodo, chloro or bromo radical which perhaloalkanes can be produced, for example, by telomerization of polyhaloolefins such as tetrafluoroethylene with a taxogen having the formula $$CF_3-CF_2I$$

if the perhaloalkans have the formula $$CF_3-CF_2-(CF_2-CF_2)_{1-4}-CF_2-CF_2I$$

By reaction with oxidizing agents these telomeric perhaloalkanes are converted to perhaloalkanoic acids such as perfluoroalkanoic acids or perfluoroalkanoic acids in which two or more of the fluoro substituents have been replaced by chloro substituents. This oxidation can be effected in an acidic medium, for example, in oleum in the presence of a catalyst, as well as in an alkaline medium with oxygen or an alkali-metal permanganate. In either case, mixtures containing perhaloalkanoic acids and unconverted perhaloalkanes are obtained.

The separation of such reaction mixtures into their components is usually beset with considerable difficulties, especially in the case of mixtures that were prepared by oxidation of mixtures containing perhaloalkanes of various chain lengths. The resulting mixtures contain not only the various perhaloalkanoic acids but also unconverted perhaloalkanes of various chain lengths. Because of the overlapping of their boiling points and vapor pressures, a satisfactory separation and purification of the perhaloalkanoic acids and perhaloalkanes from each other cannot be obtained by fractional distillation of such mixtures. Furthermore, vacuum distillation of the perhaloalkanoic acid mixture is also not a suitable procedure for this purpose since, dependent upon the method of preparation of the mixture, water and alkali-metal salts of the perfluoroalkanoic acids which can produce vigorous foaming during the distillation may be present therein as impurities. Since the alkali-metal salts produce decomposition of perhaloalkanoic acids at elevated temperatures into olefins, carbon dioxide and alkali-metal halides, the presence of alkali-metal salts in such mixtures during their distillation may decrease the yield of the desired perhaloalkanoic acids.

Separation of such mixtures of perhaloalkanoic acids and perhaloalkanes from each other and purification of such mixtures of perhaloalkanoic acids by extraction with solvents is also difficult because of the notorious tendency of the perhaloalkanoic acids as well as their salts to form emulsions, especially when extracted with water, since the acids as well as their alkali-metal salts form stable emulsions with water that are broken only with difficulty. Such emulsions also produce considerable difficulty when the perhaloalkanoic acid is extracted from an aqueous solution thereof with an organic solvent.

Perhaloalkanoic acids as such are very readily soluble in many organic solvents as are, to some extent, salts of such acids with metals and non-metals. Furthermore, perhaloalkanoic acids are themselves excellent solvents for the unconverted perhaloalkane telomers. Because of this, it is not possible to attain by extraction with organic solvents that are normally used for extractions a complete separation of the perhaloalkanoic acids from the perhaloalkanes from which they were produced.

In order to obviate these difficulties it was proposed in U.S. Pat. No. 2,904,566 granted to Edgar Fischer and German Pat. No. 1,047,764 to distill the crude acid with superheated steam while introducing gaseous hydrogen chloride or hydrogen bromide together with the steam into the distilling apparatus to prevent decomposition of the perhaloalkanoic acid. The cost of the apparatus that is required for such treatment may be high since, if metal apparatus is used, its corrosion by the hydrogen halide must be taken into consideration. Since perhaloalkanoic acids are to some extent good solvents for water, additional operating costs are required in this process to obtain anhydrous perhaloalkanoic acids.

A process is described in German Pat. No. 1,058,492 for the separation of perhaloalkanoic acids from water-insoluble components thereof, particularly long-chain perhaloalkanes, by use of formic acid containing up to 90% and preferably between 0 and 50% by weight of water. In order to prevent boiling, the extraction is performed at superatmospheric pressure and temperatures under 100° C. A disadvantage of this process is that costly pressure apparatus is required.

SUMMARY OF THE INVENTION

The principal object of the present invention is to provide a process for the separation and purification of perhaloalkanoic acids or mixtures of perhaloalkanoic acids having the general formula $$A-(CFX-CFY)_n-CFX-COOH$$

in which A is a perfluoromethyl, perfluoroethyl, perfluoropropyl or perfluoroisopropyl radical, X is a fluoro or a trifluoromethyl radical, Y is a fluoro or chloro radical and n is an integer from 1 to 4, from mixtures containing such perhaloalkanoic acids and a perfluoroalkane or mixtures of perfluoroalkanes having the general formula $$A-(CFX-CFY)_n-CFX-CFYZ$$

in which A, X, Y and n have the same significance as in the foregoing formula and Z is an iodo, chloro or bromo radical. This object is accomplished in accordance with the processes of the present invention by chromatographic separation of the mixture upon silica gel particles and eluting the perhaloalkanes adsorbed on the particles with a weakly polar eluent and subsequently eluting the perhaloalkanoic acids with a strongly polar eluent. Preferably, the separation is carried out in a chromatographic column.

In practicing the processes of the present invention, the crude mixture containing the perhaloalkanoic acid is passed into a chromatographic column loaded with a chromatography-grade silica gel. If the crude mixture is liquid, it is charged or applied directly as such to the column. Solid or wax-like mixtures, however, are first dissolved in a small volume of a weakly polar solvent before being charged onto the column. It is thus to be noted that the combined crude mixture of acids is charged to the column in the form of a liquid or solution because the individual components of the mixture would otherwise be incompletely eluted from the silica gel if they were not uniformly adsorbed by the gel before elution.

After the liquid or solution of the crude mixture of perhaloalkanoic acids penetrates into and is adsorbed on the silica gel in the column, the column or silica gel therein is eluted with a weakly polar eluent which elutes the perhaloalkanes. Eluents which are especially suitable for this purpose are chlorofluoroalkanes, preferably 1,1,2-trichloro-1,2,2-trifluoroethane and trichlorofluoromethane, as well as petroleum ether. However, other eluents, such as tetrachloromethane, chloroform and benzene are also suitable for this purpose.

After completion of the elution of the perhaloalkanes, the column or silica gel therein is eluted with a strongly polar solvent. The eluate thus collected contains the perhaloalkanoic acids in a high degree of purity. Especially suitable eluents for this purpose are ethyl acetate, diethyl ether, acetone, and methanol.

In general, the eluents which are most suitable for use in accordance with the processes of the present invention must have a high selectivity for either the perhaloalkanoic acid or for the perhaloalkane and the lowest possible boiling point so that the eluted compounds that are dissolved therein can be completely separated therefrom without any substantial loss (b.p. between 20° and 90° C).

Good separations of perhaloalkanoic acids from perhaloalkanes have been effected in accordance with the processes of the present invention with commerically available chromatography-grades of silica gel adsorbents or carriers. Surprisingly an excellent separation is obtained even when the ratio by weight of the silica gel stationary phase to the crude acid mixture is between 2:1 and 5:1, and especially between 3:1 and 4:1.

The compositions of the mixture of crude perhaloalkanoic acids can vary within a wide range, without the effectiveness of the separation being affected detrimentally. The perhaloalkane content of the crude perhaloalkanoic acid can be between 2 and 98% by weight of the mixture, and the purity of the perhaloalkanoic acid thus isolated will generally be greater than 99.5%.

A specific advantage that is inherent in the processes of the present invention is the capability of reusing the adsorbent silica gel and eluents. The silica gel can be reused two or three times without regeneration. After the silica gel has lost a significant portion of its activity, it may be sufficiently reactivated by rinsing, preferably with 1,1,2-trichloro-1,2,2-trifluoroethane, and subsequent heating at a temperature between 100° and 200° C, preferably between 140° and 150° C. After such heat-treatment, the activity of the silica gel is restored practically to its initial activity for use in the separation of perhaloalkanoic acids. In this manner, the silica gel can be used for separations of additional batches of the perfluoroalkanoic acids.

The processes of the present invention are not only suitable for the purification of laboratory-size batches of crude perhaloalkanoic acids and mixtures thereof but can also be used successfully on a commercial or plant scale. Even when used in such large-scale operations, perhaloalkanoic acids having a very high degree of purity can be produced. All components of the crude mixture of perhaloalkanoic acids can be recovered substantially completely in accordance with the separation procedures of the present invention. The expensive perhaloalkanes can also thus be recovered and recycled to produce additional quantities of perhaloalkanoic acids.

DETAILED DESCRIPTION AND PREFERRED EMBODIMENTS OF THE INVENTION

The invention is further described in the Examples which follow which were selected solely for purposes of illustration and consequently are not to be construed as limiting the invention.

In all Examples which follow, except Example 23, a telomeric mixture of crude perfluoroalkyl iodides and a mixture of crude perfluoroalkanoic acids were used. The mixture of crude perfluoroalkanoic acids was prepared from a mixture of telomeric perfluoroalkyl iodides which had the formula $$CF_3CF_2(CF_2CF_2)_nCF_2CF_2I$$

in which formula n is the integers from 1 to 4. The mixture of telomeric perfluoroalkyl iodides was oxidized by reaction at an elevated temperature with oleum and chlorine in the presence of zinc sulfate as described in our U.S. patent application Ser. No. 329,188, filed Feb. 2, 1973, now Patent 3,862,971, to produce the liquid that was used containing about 99% by weight of perfluoroalkanoic acids having the formula $$CF_3CF_2(CF_2CF_2)_nCF_2COOH$$

in which formula n is also the integers from 1 to 4, which perfluoroalkanoic acids had an average molecular weight of 570.

A glass chromatographic column was used in all Examples, except Example 24. This column had a length of 62.0 centimeters and an internal diameter of 2.0 centimeters and was provided with a stationary porous fritted glass filter disc and stop cock and was loaded with specified amounts of a chromatography-grade silica gel particles such as are available from Firma Woelm.

EXAMPLE 1

Into the chromatographic column that was described hereinbefore, which was loaded with 60 grams of chromatography-grade silica gel particles, was charged 20 grams of mixture of equal parts by weight of the perfluoroalkyl iodide telomers and the crude liquid mixture of perfluoroalkanoic acids that were described hereinbefore, and the adsorbed telomeric perfluoroalkyl iodides were then eluted from the silica gel with four 50-milliliter portions of 1,1,2-trichloro-1,2,2-trifluoroethane. Thereafter the perfluoroalkanoic acids were eluted from the silica gel with 250 milliliters of diethyl ether. The eluted fractions in the eluates were recovered by distillation of the eluate therefrom. The residue of the diethyl ether eluate consisted of 10.2 grams of perfluoroalkanoic acids. Since 10.2 grams is equivalent to a yield of more than 100% of the acids, the excess may be attributed to eluent that was still retained by the substance eluted. In this and in other examples, in which recoveries of more than 100% are example is entered in the first column of this Table. In the second column are entered the volumes of the eluents that were used in milliliters in the first elution (Eluent I) of the silica gel, while the eluent and volume thereof that was used in the second elution of the silica gel (Eluent II) is entered in the third column. The recoveries of the perfluoroalkyl iodide telomers and perfluoroalkanoic acids are referred to in the headings of the Table as "iodides" and "acids", respectively, and the total percentage recovery of both, based upon the total amount of iodides and acids charged, are entered in the last columns under the heading "Efficiency". In all examples of this series, the purity of the recovered acids was approximately 99%.

Table I

| Example No. | Eluent I, ml | Eluent II, ml | Recovery Iodides g | % | Acids g | % | Efficiency % |
|---|---|---|---|---|---|---|---|
| 1 | 1,1,2-Trichloro-1,2,2-trifluoroethane 200 | Diethyl ether 250 | 10.2 | 100 | 9.9 | 99 | 100 |
| 2 | Petroleum ether 250 | Acetone 200 | 9.1 | 91 | 8.8 | 88 | 89 |
| 3 | Carbon tetrachloride 200 | Acetone 250 | 5.4 | 54 | 8.7 | 87 | 71 |
| 4 | Benzene 200 | Acetone 250 | 4.4 | 44 | 10.8 | 100 | 72 |
| 5 | Chloroform 200 | Acetone 250 | 3.0 | 30 | 9.4 | 94 | 62 |
| 6 | Petroleum ether 250 | Methanol 250 | 6.8 | 68 | 7.7 | 77 | 73 |
| 7 | Petroleum ether 250 | Ethyl acetate 250 | 9.7 | 97 | 10.0 | 100 | 99 |
| 8 | 1,1,2-Trichloro-1,2,2-trifluoroethane 200 | Ethyl acetate 250 | 9.8 | 98 | 10.0 | 100 | 100 |
| 9 | Petroleum ether 250 | Diethyl ether 250 | 9.2 | 92 | 9.8 | 98 | 95 | reported, the excess may be attributable to eluent that was still retained by the substance eluted. From the 1,1,2-trichloro-1,2,2-trifluoroethane eluate, 9.9 grams, which is equivalent to 99% of the original amount of perfluoroalkyl iodides, was obtained. Each of the recovered components had a purity of more than 99%.

EXAMPLES 2–9

In this series of examples, the procedure described in Example 1 was repeated but different solvents were used in the two elution steps. Preselected volumes of 1,1,2-trichloro-1,2,2-trifluoroethane, petroleum ether, tetrachloromethane, benzene and chloroform were each used for elution of the perfluoroalkanes in the first step. In the second elution step, preselected volumes of respectively each of acetone, methanol, ethyl acetate, and diethyl ether were used for elution of the perfluoroalkanoic acids.

The recovery of perfluoroalkyl iodides in each of the first elution steps and the recovery of perfluoroalkanoic acids in each of the second elution steps, in terms of both grams by weight and percentages are entered in Table I which follows. The number of the respective

EXAMPLES 10–15

In this series of examples, the chromatographic column was loaded with 90 grams of silica gel and was charged with 30 grams of a liquid mixture of the telomeric perfluoroalkyl iodides and perfluoroalkanoic acids in various ratios. The ratio of the liquid mixture to silica gel was 3:1, as in the preceding examples. The weight ratio of the iodides to the acids was varied between a ratio of 1:9 and 19:1. The eluents that were used were the same as were used in Example 1, namely, 1,1,2-trichloro-1,2,2-trifluoroethane and diethyl ether, but their amounts were varied. In all other respects the procedure described in Example 1 was repeated. The amounts and percentages of the perfluoroalkanoic acids that were recovered in these examples are entered in Table II which follows.

Table II

| Example No. | Composition of mixture Iodides, g | Acids, g | Amounts of eluents used Eluent I, ml | Eluent II, ml | g | Acids recovered % |
|---|---|---|---|---|---|---|
| 10 | 3 | 27 | 300 | 100 | 3.1 | 103 |
| 11 | 6 | 24 | 300 | 200 | 6.1 | 102 |
| 12 | 15 | 15 | 300 | 200 | 15.4 | 103 |
| 13 | 24 | 6 | 230 | 400 | 24.9 | 103 |
| 14 | 27 | 3 | 150 | 400 | 27.2 | 101 |
| 15 | 28.5 | 1.5 | 140 | 400 | 28.5 | 100 | fluoroalkanoic acids.

EXAMPLES 16–18

In each example of this series, the liquid mixture with which the column was charged consisted of 6 grams of telomeric perfluoroalkyl iodides and 24 grams of perfluoroalkanoic acids, but the amounts of eluents, which were the same as were used in Example 1, and the amount of silica gel were varied, but in all other respects the procedure described in Example 1 was repeated. The results are entered in Table III which follows. The ratio of silica gel to mixture that is entered in the third column of this Table refers to the ratio by weight of the silica gel in the column to the total weight of the original mixture of iodides and acids with which the column was initially charged.

Table III

| Example No. | Silica gel, g | Ratio of silica gel to mixture | eluents used, ml | | Acids recovered | |
|---|---|---|---|---|---|---|
| | | | Eluent I | Eluent II | g | % |
| 16 | 60 | 2:1 | 135 | 350 | 23.1 | 96 |
| 17 | 90 | 3:1 | 230 | 400 | 24.9 | 102 |
| 18 | 150 | 5:1 | 540 | 400 | 25.2 | 105 |

In these examples, the recovered acids had a purity of approximately 99%.

EXAMPLES 19–21

In this series of examples, the column was charged with 30 grams of the same mixture of iodides and acids that were used in Examples 16 to 18, but the same 90 grams of silica gel was reused successively, being washed each time before reuse in the succeeding example with 200 milliliters of 1,1,2-trichloro-1,2,2-trifluoroethane. The eluents that were used in Example 1 were used in these examples but their amounts were varied. The results are entered in Table IV which follows. The efficiency percentage that is entered in the last column is based upon the total amounts of both the iodides and acids in the original mixture that were recovered. The percentage of acids recovered is based, as in the prior examples, upon the total amount of acids that were originally present in the mixture.

Table IV

| Example No. | Amounts of eluent used | | Acids recovered | | Efficiency % |
|---|---|---|---|---|---|
| | Eluent I, ml | Eluent II, ml | g | % | |
| 19 | 140 | 150 | 24.1 | 100 | 100 |
| 20 | 100 | 400 | 25.8 | 108 | 100 |
| 21 | 110 | 300 | 15.9 | 66 | 66 |

EXAMPLE 22

The 90 grams of silica gel in the preceding Example 21 that had been successively used three times for the chromatographic separation as described therein, was washed a third time with 200 milliliters of 1,1,2-trichloro-1,2,2-trifluoroethane and then heated in a drying oven at a temperature of 150° C for two hours. The column was then loaded with the thus-treated silica gel and charged with a mixture of 27 grams of the perfluoroalkanoic acids and 3 grams of the telomeric perfluoroalkyl iodides that were described hereinbefore and eluted first with 150 milliliters of 1,1,2-trichloro-1,2,2-trifluoroethane and then with 350 milliliters of diethyl ether and the eluents were distilled from the two eluates thus obtained. In this manner, 27.0 grams, corresponding to a yield of 100%, of the perfluoroalkanoic acids, which had a purity of 99.5%, was obtained, together with 2.9 grams, corresponding to a yield of 96.7%, of the telomeric perfluoroalkyl iodides.

EXAMPLE 23

In this example, the chromatographic column was loaded with 60 grams of chromatography-grade silica gel and then charged with 20 grams of a mixture of equal parts by weight of a crude mixture of perhaloalkanoic acids having an average molecular weight of 618 and conforming to the general formula

$CF_3CF_2(CF_2CFCl)_nCF_2COOH$ in which formula $n$ is the integers from 1 to 4. The crude telomeric mixture of acids was made by oxidation in accordance with the process described in application Ser. No. 329,188, now U.S. Pat. No. 3,862,971, of a telomeric mixture of perhaloalkyl iodides having the formula

$CF_3CF_2(CF_2CFCl)_nCF_2CFClI$ is which formula n is also the integers from 1 to 4 that was prepared by telomerization of pentafluoromonoiodoethane ($CF_3CF_2I$) with chlorotrifluoroethylene.

The silica gel upon which the mixture of crude acids was adsorbed was then eluted with a four 50 milliliters portions of 1,1,2-trichloro-1,2,2-trifluoroethane and subsequently with 250 milliliters of diethyl ether and the eluents were distilled from each of the two eluates. In this manner, 9.9 grams of the mixture of perhaloalkanoic acids, equivalent to 99% of the amount that was present in the original mixture, and 9.8 grams of perhaloalkyl iodides, equivalent to 98% of the amount that was present in the original mixture, were obtained. The purified mixture of perhaloalkanoic acids thus obtained contained less than 0.5% of telomeric perhaloalkyl iodides.

EXAMPLE 24

In this example, a chromatographic column was used which had a length of 100 centimeters and an internal diameter of 5 centimeters which was loaded with 600 grams of chromatography-grade silica gel. The column was charged with a solution of 190 grams of a mixture of crude perfluoroalkanoic acids prepared from a telomeric mixture of perfluoroalkyl iodides in accordance with the process described in our application Serial No. 329,188 that was referred to hereinbefore, dissolved in a minimum amount of 1,1,2-trichloro-1,2,2-trifluoroethane. After elution of the silica gel with 400 milliliters of 1,1,2-trichloro-1,2,2-trifluoroethane and distillation of the eluent from the eluate thus obtained, 10 grams of telomeric perfluoroalkyl iodides was recovered. The silica gel was then eluted with 1800 milliliters of diethyl ether, and the eluent was then distilled from the eluate, leaving 178 grams of perfluoroalkanoic acids having a purity of 99.4%. From the 190 grams of original mixture of crude acids and iodides, 188 grams was accordingly recovered, which corresponds to a recovery of 99% of the original.

Without further analysis, the foregoing will so fully reveal the gist of the present invention that others can by applying current knowledge readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. A process for the separation and purification of a perhaloalkanoic acid or mixture of perhaloalkanoic acids having the formula $$A-(CFX-CFY)_n-CFX-COOH$$

in which A is a perfluoromethyl, perfluoroethyl, perfluoropropyl or perfluoroisopropyl radical, X is a fluoro or a trifluoromethyl radical, Y is a fluoro or chloro radical and n is an integer from 1 to 4, from a mixture containing the said acid or mixture of acids and a perhaloalkane or mixture of perhaloalkanes having the formula $$A-(CFX-CFY)_n-CFX-CFYZ$$

in which formula A, X, Y and n have the same significance as hereinbefore, and Z is an iodo, chloro or bromo radical, which comprises adsorbing the said mixture in the form of a liquid upon a chromatographic column of adsorbent silica gel particles and subsequently eluting the perhaloalkane or perhaloalkanes therefrom first with a weakly polar eluent selected from the group consisting of chlorofluoroalkanes, tetrachloromethane, chloroform, benzene and petroleum ether, and then with a strongly polar eluent selected from the group consisting of ethyl acetate, diethyl ether, acetone and methanol.

2. A process as described in claim 1 in which the ratio by weight of the silica gel adsorbent particles to the mixture containing the perhaloalkanoic acids before the adsorbent is eluted is between 2:1 and 5:1.

3. A process as defined in claim 1 in which the ratio by weight of the silica gel adsorbent particles to the mixture containing the perhaloalkanoic acids before the adsorbent is eluted is between 3:1 and 4:1.

4. A process as defined in claim 1 in which the silica gel adsorbent particles are reactivated by rinsing with 1,1,2-trichloro-1,2,2-trifluoroethane and subsequent heating at a temperature between 140° and 150° C.

5. A process as defined in claim 1 in which the eluent for the perhaloalkanes is 1,1,2-trichloro-1,2,2-trifluoroethane.

6. A process as defined in claim 1 in which the eluent for the perfluoroalkanoic acids is diethyl ether.

* * * * *